(12) United States Patent
Lee (10) Patent No.: US 12,144,639 B2
(45) Date of Patent: Nov. 19, 2024

(54) METHOD FOR SCREENING PSYCHIATRIC DISORDER BASED ON CONVERSATION AND APPARATUS THEREFOR

(71) Applicant: SEOUL NATIONAL UNIVERSITY R&DB FOUNDATION, Seoul (KR)

(72) Inventor: Jun Young Lee, Seoul (KR)

(73) Assignee: EMOCOG Co., Ltd., Seoul (KR)

( * ) Notice: Subject to any disclaimer, the term of this patent is extended or adjusted under 35 U.S.C. 154(b) by 641 days.

(21) Appl. No.: 17/374,831

(22) Filed: Jul. 13, 2021

(65) Prior Publication Data

US 2022/0015687 A1     Jan. 20, 2022

(30) Foreign Application Priority Data

Jul. 15, 2020   (KR) .................. 10-2020-0087533

(51) Int. Cl.
   *A61B 5/00*     (2006.01)
   *A61B 5/16*     (2006.01)
   *G10L 25/66*    (2013.01)

(52) U.S. Cl.
   CPC ............ *A61B 5/4088* (2013.01); *A61B 5/165* (2013.01); *G10L 25/66* (2013.01)

(58) Field of Classification Search
   CPC ..... A61B 5/4088; A61B 5/165; A61B 5/4803; A61B 5/16; A61B 5/4884; G10L 25/66; G16H 10/20; G16H 20/70; G16H 40/67; G16H 50/30
   See application file for complete search history.

(56) References Cited

U.S. PATENT DOCUMENTS

| | | |
|---|---|---|
| 2017/0119302 A1 | 5/2017 | Rosenbek et al. |
| 2018/0078184 A1* | 3/2018 | Yagi ..................... A61B 5/1128 |
| 2019/0043619 A1* | 2/2019 | Vaughan ................ G16H 20/70 |
| 2021/0110895 A1* | 4/2021 | Shriberg ................. G06F 40/20 |
| 2023/0154575 A1* | 5/2023 | Goel ....................... G16H 10/20 705/3 |
| 2023/0187064 A1* | 6/2023 | Pittman .................. G16H 50/30 705/2 |

FOREIGN PATENT DOCUMENTS

| | | |
|---|---|---|
| JP | 2007282992 A | 11/2007 |
| JP | 2018015139 A | 2/2018 |

(Continued)

OTHER PUBLICATIONS

Extended European Search Report of EP Patent Application No. 21841856.4 dated Jul. 7, 2023.

(Continued)

*Primary Examiner* — Jeffrey S Vanderveen
(74) *Attorney, Agent, or Firm* — Dinsmore & Shohl LLP; Yongsok Choi, Esq.

(57) ABSTRACT

Disclosed are a psychiatric disorder screening method and apparatus based on conversation. The psychiatric disorder screening apparatus outputs stimulation including at least one of a story, a word, a sound, a picture, a motion, a color or a direction, and when receiving a response to the stimulation from a testee, determines the presence or absence of a psychiatric disorder by comparing a correct answer ratio of the response or a voice feature included in the response with correct answer ratios or voice features of a normal group and a disease group.

7 Claims, 6 Drawing Sheets

(56) References Cited

FOREIGN PATENT DOCUMENTS

| | | |
|---|---|---|
| KR | 10-2012-0070668 A | 7/2012 |
| KR | 10-2018-0068611 A | 6/2018 |
| KR | 10-2019-0081626 A | 7/2019 |
| KR | 10-2020-0010920 A | 1/2020 |
| KR | 10-2064681 B1 | 1/2020 |
| WO | 2019081915 A1 | 5/2019 |
| WO | 2020013302 A1 | 1/2020 |

OTHER PUBLICATIONS

Japanese Office Action on JP Patent Application No. 2023-502573 dated Nov. 21, 2023.

* cited by examiner

| Example of dementia screening test story |
|---|
| Now, here is a short story about the tale of Heungbu adapted for memory ability.<br>Please listen up and imagine the scene.<br>You will memorize the story and answer questions later.<br>Let's get started. |
| Once upon a time, Mr. Yeon has two sons Ondal, greedy older brother, and Heungbu, good younger brother.<br>The older brother got all inheritance and became rich, but gave nothing to Heungbu.<br>Poor Heungbu asked something to eat to his sister-in-law, but she rejected and slapped him in the face with a round plate.<br>Heungbu found the noodle on his cheek and ate it, and asked her to strike the other cheek as well, but she did not help him.<br>One day, an injured sparrow came to Heungbu's.<br>Warm-hearted Heungbu looked into the wing and took good care of it.<br>The recovered sparrow gave him yellow sunflower seeds in return and has gone.<br>In autumn, sapphire was produced from the seeds planted in spring and Heungbu became very rich.<br><br>Well, we can be rich in memory.<br>Here are seven questions to see how much you can memorize the story.<br>Please answer the questions. |

[FIG. 6]

| | |
|---|---|
| What is the name of greedy older brother? | 1: Ondal     2: Galdeung<br>3: Oseong    4: Nolbu |
| What did the sister-in-law slap Heungbu in the face with? | 1: Spoon     2: Bowl<br>3: Plate       4: Ladle |
| What did Heungbu find on his cheek? | 1: Dough soup   2: Noodle<br>3: Rice cake     4: Grains of rice |
| What type of injured animal did come to Heungbu's? | 1: Sparrow    2: Chick<br>3: Maggie     4: Swallow |
| What body part of the animal was injured? | 1: Belly     2: Ear<br>3: Leg      4: Wing |
| What did the animal give to Heungbu in return? | 1: Sunflower seed   2: Corn seed<br>3: Peanut seed      4: Gourd seed |
| What was produced from the seed in autumn? | 1: Gold, silver treasure   2: Sapphire<br>3: Pearl                     4: Emerald |
| How many questions do you think you have correct answers to the seven questions? | 1: Seven     2: Six<br>3: Five       4: Four or smaller |

[FIG. 7]

METHOD FOR SCREENING PSYCHIATRIC DISORDER BASED ON CONVERSATION AND APPARATUS THEREFOR

TECHNICAL FIELD

The embodiments of the present disclosure relate to a psychiatric disorder screening method and apparatus through conversation. This application claims priority to Korean Patent Application No. 10-2020-0087533, filed on Jul. 15, 2020, and all the benefits accruing therefrom under 35 U.S.C. § 119, the contents of which in its entirety are herein incorporated by reference.

BACKGROUND ART

Currently, psychiatric disorder (for example, dementia, attention deficit disorders, learning disorders, schizophrenia, mood disorders, additive disorders, etc.) tests are performed by experts at particular spaces and particular times. Accordingly, a person who wants to get tested for psychiatric disorders has to book the test and visit a particular place such as a hospital at the appointed time, causing inconvenience.

DISCLOSURE

Technical Problem

The embodiments of the present disclosure are directed to providing a psychiatric disorder screening method and apparatus based on conversation in a convenient manner from anywhere, for example, at home, not in a hospital, without temporal and spatial limitations.

Technical Solution

To achieve the above-described object, an example of a psychiatric disorder screening method based on conversation according to an embodiment of the present disclosure includes outputting stimulation including at least one of a story, a word, a sound, a picture, a motion, a color or a direction, receiving a response to the stimulation from a testee, and determining the presence or absence of a psychiatric disorder by comparing a correct answer ratio of the response or a voice feature included in the response with correct answer ratios or voice features of a normal group and a disease group, or analyzing conversation details.

To achieve the above-described object, an example of a psychiatric disorder screening apparatus based on conversation according to an embodiment of the present disclosure includes a data output unit to output stimulation including at least one of a story, a word, a sound, a picture, a motion, a color or a direction, a voice input unit to receive a response to the stimulation from a testee, and a voice/conversation analysis unit to determine the presence or absence of a psychiatric disorder by comparing a correct answer ratio of the response or a voice feature included in the response with correct answer ratios or voice features of a normal group and a disease group, or analyzing conversation details.

To achieve the above-described object, an example of a recording medium according to an embodiment of the present disclosure is a computer-readable recording medium having computer-readable instructions stored thereon, the instructions being executed by at least one processor to enable the at least one processor to perform the steps of outputting stimulation including at least one of a story, a word, a sound, a picture, a motion, a color or a direction, receiving a response to the stimulation from a testee, and determining the presence or absence of a psychiatric disorder by comparing a correct answer ratio of the response or a voice feature included in the response with correct answer ratios or voice features of a normal group and a disease group, or analyzing conversation details.

Advantageous Effects

According to an embodiment of the present disclosure, it is possible to get tested for psychiatric disorders based on conversation in a convenient space, for example, at home, without needing to visit a hospital. In addition, it is possible to improve the psychiatric disorder screening accuracy by making use of conversation details and voice data together.

BEST MODE

Hereinafter, a psychiatric disorder screening method and apparatus based on conversation according to an embodiment of the present disclosure will be described in detail with reference to the accompanying drawings.

Figure 1:
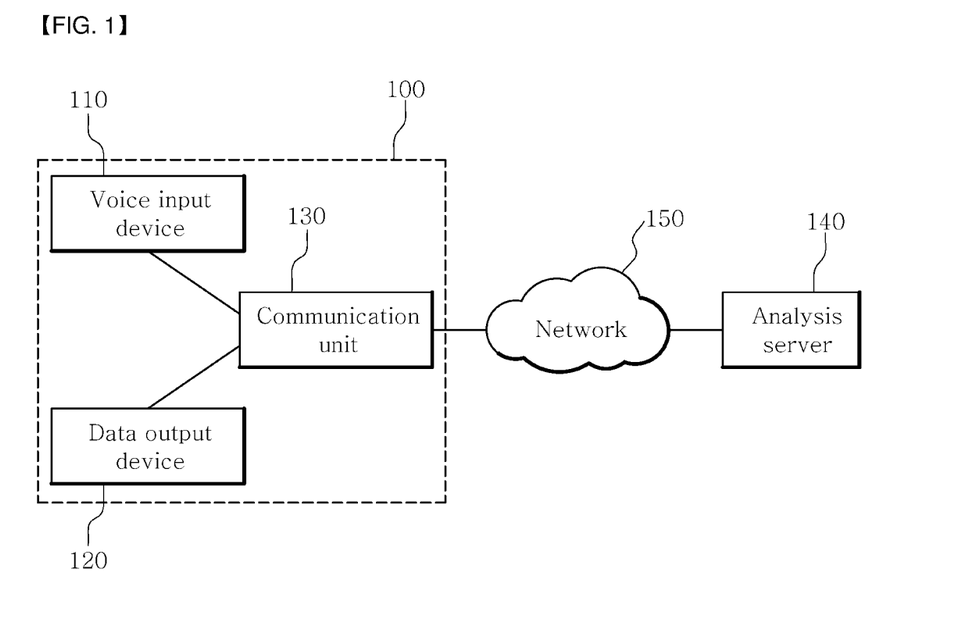
FIG. 1 shows an example of a schematic entire architecture of a system which implements a psychiatric disorder screening method according to an embodiment of the present disclosure.

FIG. 1 is a diagram showing an example of a schematic entire architecture of a system which implements a psychiatric disorder screening method according to an embodiment of the present disclosure.

Referring to FIG. 1, the system for psychiatric disorder screening largely includes a user terminal 100 and an analysis server 140. The user terminal 100 and the analysis server 140 may be connected via a network 150, for example, a wired network or a wireless network.

The user terminal 100 includes a voice input device 110, a data output device 120 and a communication unit 130. Here, the voice input device 110 refers to a device capable of receiving an input sound such as a microphone, the data output device 120 refers to a speaker which outputs a sound or a display which outputs an image, and the communication unit 130 refers to a variety of communication modules capable of transmitting/receiving data to/from the analysis server 140. The user terminal 100 may further include a variety of components necessary to realize this embodiment, for example, a processor, a memory, etc. However, for convenience of description, this embodiment chiefly shows the components necessary for psychiatric disorder screening.

In this embodiment, the user terminal 100 includes any terminal including the voice input device 110, the data output device 120 and the communication unit 130, and is not limited to a particular device that may be implemented as a computer, a tablet PC, a smartphone, a smart refrigerator, a smart TV, an AI speaker, various types of Internet Of Things (IoT) devices.

The analysis server 140 is a device which determines whether a testee has a psychiatric disorder (for example, dementia) by analyzing data received from the user terminal 100. The analysis server 140 is not limited to the term 'server', and may be implemented as not only a server but also a computer or a cloud system.

Although this embodiment shows the user terminal 100 and the analysis server 140 connected via the network 150 for psychiatric disorder screening, the present disclosure is not necessarily limited thereto. For example, some or all the functions of the analysis server 140 may be performed by the user terminal 100. In case that all the functions of the analysis server 140 are performed by the user terminal 100, the analysis server 140 may be omitted. That is, the user terminal 100 may perform psychiatric disorder screening and display the results without the analysis server 140. However, for convenience of description, the present disclosure is described based on the structure of this embodiment in which the user terminal 100 and the analysis server 140 are connected via the network 150.

Figure 2:
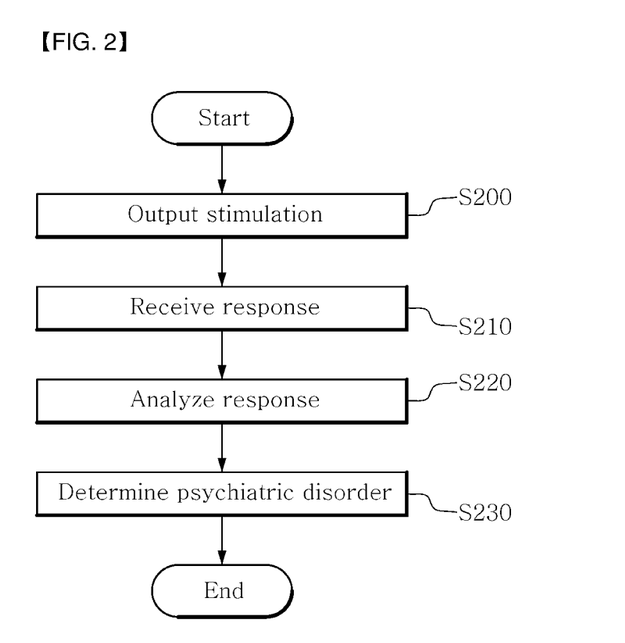
FIG. 2 is a flowchart showing an example of a psychiatric disorder screening method according to an embodiment of the present disclosure.

FIG. 2 is a flowchart showing an example of the psychiatric disorder screening method according to an embodiment of the present disclosure.

Figure 5:
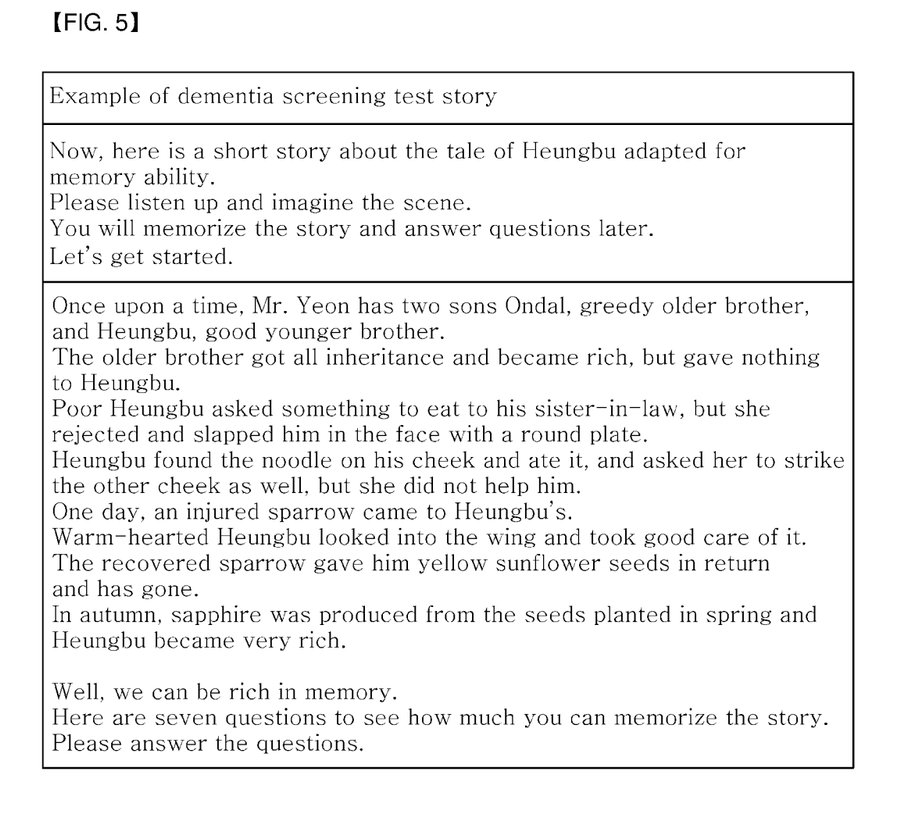
FIGS. 5 and 6 show an example of story stimulation used for psychiatric disorder screening according to an embodiment of the present disclosure.
Figure 6:
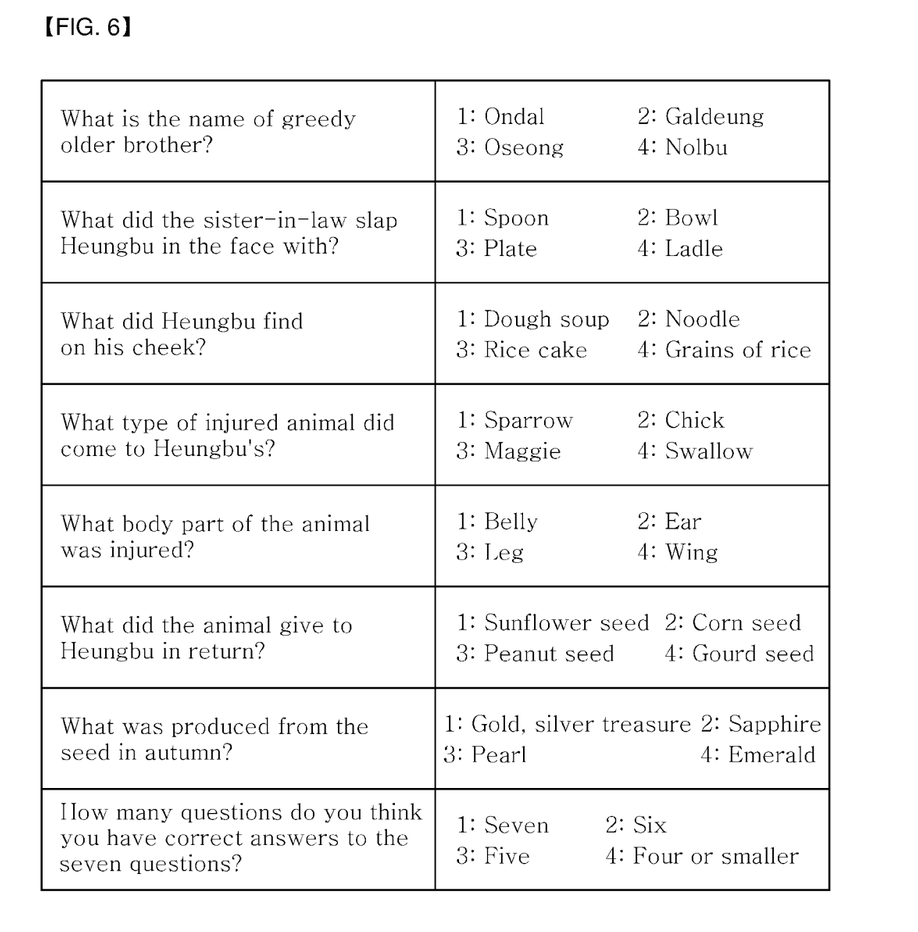

Referring to FIGS. 1 and 2, the user terminal 100 outputs stimulation through the data output device 120 (S200). Here, the stimulation refers to a story, a sound or an image that may stimulate the testee's visual or auditory sense. For example, the stimulation may include at least one of a story, a word, a sound, a picture, a motion, a color or a direction. FIGS. 5 and 6 show an example of story stimulation.

In an embodiment, the user terminal 100 may receive stimulation details from the analysis server 140 in real time and output them through the data output device 120, or may output stimulation details pre-stored in the user terminal.

In another embodiment, interference stimulation may be placed in the stimulus or between the stimuli outputted through the data output device 120. Here, the interference stimulation is stimulation for giving confusion to the testee to increase a response difference between a normal group and a disease group in order to increase the psychiatric disorder screening accuracy. For example, in the case of the story stimulation of FIG. 5, an unfamiliar word or situation may be outputted instead of a familiar word or situation in a familiar story, and the generated word or situation corresponds to the interference stimulation. The location and details of the interference stimulation may be predefined for each stimulus. In another example, the interference stimulation such as another story, sound or picture may be outputted before asking questions to the testee, or rest intervals of a predetermined period of time may be given between the stimuli to erase the memory of the previous stimulation before the testee answers the questions.

In still another embodiment, the user terminal 100 may output stimulation with details changed depending on the testee's response in real time. The stimulation details changed in real time may be selected by the user terminal 100, or the testee's response may be provided to the analysis server 140 in real time and stimulation changed in real time may be received from the analysis server 140 and outputted. For example, when the correct answer ratio of the testee's response to the question in the story stimulation of FIGS. 5 and 6 is equal to or larger than a predetermined value, more difficult story stimulation may be outputted or a different type of stimulation such as a sound or an image may be outputted. The type of next output stimulation may be predefined according to the testee's correct answer ratio.

The user terminal 100 receives the testee's response to the stimulation through the voice input device 110 (S210). For example, the stimulation may be story stimulation as shown in FIG. 5, and in this case, the user terminal 100 may output the story through the data output device 120 either audibly or visually, or both. After the user terminal 100 outputs the stimulation, the user terminal 100 may ask the question as shown in FIG. 6 and receive the testee's response through the voice input device 110.

The user terminal 100 may perform the process of outputting stimulation and receiving the testee's response to the stimulation in a repeated manner with varying stimulation. For example, the user terminal 100 may output first stimulation and receive the testee's response to the first stimulation, and output second stimulation and receive the testee's response to the second stimulation. That is, the user terminal may perform the test in a manner of making conversation with the testee, and to this end, an AI speaker or various types of smart devices may be used in this embodiment.

Figure 3:
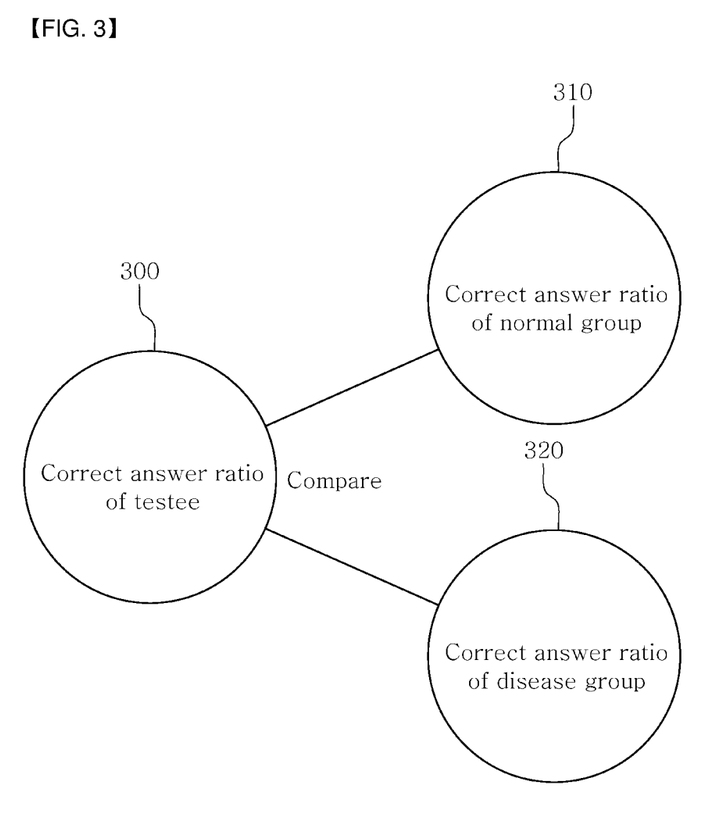
FIG. 3 shows an example of a method for psychiatric disorder screening based on a testee's correct answer ratio according to an embodiment of the present disclosure.
Figure 4:
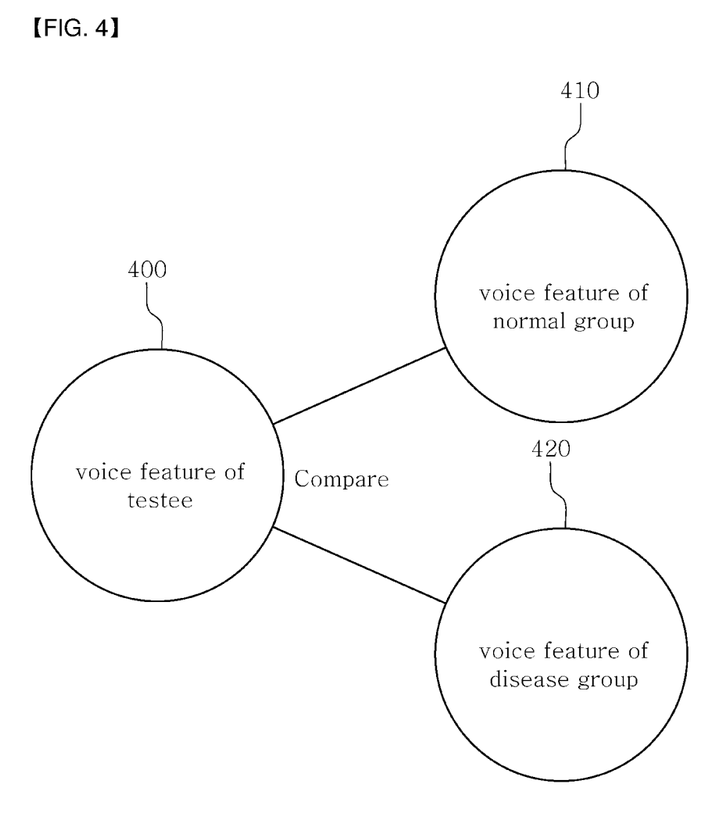
FIG. 4 shows an example of a method for psychiatric disorder screening based on a testee's voice feature according to an embodiment of the present disclosure.

The user terminal 100 transmits the input response from the testee to the analysis server 140, and the analysis server 140 determines the presence or absence of a psychiatric disorder by analyzing the testee's response (S220, S230). Specifically, the analysis server 140 may determine the presence or absence of a psychiatric disorder by analyzing which of the normal group or the disease group the correct answer ratio of the testee's response to the stimulation and/or the testee's voice feature is closer to by analysis of the testee's response details. FIG. 3 shows an example of psychiatric disorder screening based on the testee's correct answer ratio, and FIG. 4 shows an example of psychiatric disorder screening based on the testee's voice feature. In another example, the analysis server 140 may consider the number of words included in the testee's response, the sentence completion level, the use or non-use of low frequency words, the level of comprehension of ambiguous or vague sentences and the usage frequency of feeling words when determining the presence or absence of a psychiatric disorder.

When the psychiatric disorder analysis is completed, the analysis server 140 may provide the psychiatric disorder screening result to the user terminal 100 or a predefined terminal (for example, a terminal of a caregiver or a medical staff for the testee).

FIG. 3 is a diagram showing an example of a method for psychiatric disorder screening based on the testee's correct answer ratio according to an embodiment of the present disclosure.

Referring to FIG. 3, the analysis server 140 identifies the testee's correct answer ratio 300 to the stimulation and compares it with correct answer ratios 310, 320 of the normal group and the disease group. In the case of the story stimulation of FIGS. 5 and 6, the analysis server 140 may identify the testee's response for each question details by analyzing the testee's response by a variety of existing voice recognition technologies, and determine if the response is a correct answer. When stimuli are outputted to the testee, the analysis server may determine whether the response is a correct answer for each stimulus.

For example, when the correct answer ratio 310 of the normal group and the correct answer ratio 320 of the disease group with dementia are defined for the story stimulation of FIGS. 5 and 6, the analysis server 140 may identify whether the testee has dementia by identifying which of the normal group or the disease group the testee's correct answer ratio 300 is closer to. That is, in case that the correct answer ratio of the normal group is 70% and the correct answer ratio of the disease group is 30%, when the testee's correct answer ratio is 20%, since the testee's correct answer ratio is lower than that of the disease group, the analysis server 140 may determine that the testee gets dementia. In another example, in case that the testee's correct answer ratio is between 30% and 70%, when the testee's correct answer ratio is closer to the disease group among the normal group and the disease group, the analysis server 140 may determine the likelihood of getting dementia, and in this case, the likelihood of getting dementia may be calculated and provided as a probability according to the relative distance between the testee's correct answer ratio and the correct answer ratio of each of the normal group and the disease group.

FIG. 4 is a diagram showing an example of a method for psychiatric disorder screening based on the testee's voice feature according to an embodiment of the present disclosure.

Referring to FIG. 4, the analysis server 140 may analyze the testee's voice feature 400 and compare it with voice features 410, 420 of the normal group and the disease group. The analysis server 140 may analyze a formant, Mel-Frequency Cepstral Coefficients (MFCCs), a pitch, a sound length and a voice quality as examples of the voice feature.

The analysis server 140 pre-identifies and stores the voice feature 410 of the normal group and the voice feature 420 of the disease group, and may determine whether the testee has a psychiatric disorder by identifying which of the normal group or the disease group the testee's voice feature 400 is closer to. For example, when the voice features 410, 420 of the normal group and the disease group with regard to dementia are defined based on the story stimulation of FIGS. 5 and 6, the analysis server 140 may determine the likelihood of dementia by analyzing how much the testee's voice feature 400 is close to which of the normal group or the disease group. For example, when the testee's voice feature 400 is similar to the voice feature 420 of the disease group by 80%, the analysis server 140 may output 80% likelihood of dementia.

The comparison of voice features may be performed by a variety of methods. For example, the analysis server 140 predefines values of voice features (for example, a formant, MFCCs, a pitch, etc.) to be extracted from the testee's response, and identifies the predefined values of voice features from the testee's response and creates a vector containing the values as variables. The values of voice features of the normal group and the disease group are also pre-created into a vector. The analysis server 140 may identify which of the normal group or the disease group the voice feature of the testee is more similar to by identifying a similarity (for example, Euclidean distance) between the vector of voice features of the testee and each vector of the normal group and the disease group.

In another embodiment, the analysis server 140 may analyze the conversation details and use them for psychiatric disorder screening. For example, the analysis server 140 may determine the presence or absence of a psychiatric disorder by identifying the number of words, the sentence completion level, the use of low frequency words (i.e., difficult words), the level of comprehension of ambiguous or vague sentences and the usage frequency of feeling words from the testee's response and comparing it with a pre-defined reference value for psychiatric disorder screening. For example, when the number of words is equal or less than a predefined value, the analysis server 140 may determine that the testee has a psychiatric disorder, or when the usage frequency of low frequency words is equal to or larger than a predetermined value, the analysis server 140 may determine that the testee does not have a psychiatric disorder, or when the usage frequency of feeling words is equal to or larger than a predetermined value, the analysis server 140 may determine that the testee does not have a psychiatric disorder. Alternatively, the analysis server 140 may identify the sentence completion level or the level of comprehension of ambiguous or vague sentences in the testee's response using artificial intelligence or a variety of existing sentence analysis techniques and determine the presence or absence of a psychiatric disorder based on it.

In still another embodiment, the analysis server 140 may analyze the conversation details using artificial intelligence. For example, an artificial intelligence model may be trained to classify as the normal group and the disease group through conversation with persons belonging to the normal group and conversation with persons belonging to the disease group. The analysis server 140 may determine the presence or absence of a psychiatric disorder through conversation with the testee using the trained artificial intelligence model. The artificial intelligence model may include a model capable of talking with a user such as an AI speaker. For example, the analysis server 140 may identify which of the normal group or the disease group the testee belongs to using the conversation details identified through a process of outputting a casual conversation, for example, about weather or date as stimulation through the artificial intelligence model and receiving the testee's response to the simulation.

The analysis server 140 may improve the psychiatric disorder screening accuracy by considering at least one of the testee's correct answer ratio 300 of FIG. 3, the testee's voice feature 400 of FIG. 4 or the conversation details.

FIGS. 5 and 6 are diagrams showing an example of story stimulation used for psychiatric disorder screening according to an embodiment of the present disclosure.

Referring to FIG. 5, the story stimulation includes a predefined length of story. For example, the story stimulation may be a well-known story such as the Tale of Heungbu. When outputting the story stimulation for psychiatric disorder screening, the user terminal 100 may output the story as it is, or change a particular word to a predefined other word. For example, in the Tale of Heungbu in which Heungbu got slapped in the face with a ladle, an unfamiliar 'plate' may be outputted instead of the familiar word 'ladle' to maximize interference of dementia patients.

Referring to FIG. 6, the user terminal 100 may receive responses to the story stimulation from the testee through questions.

Figure 7:
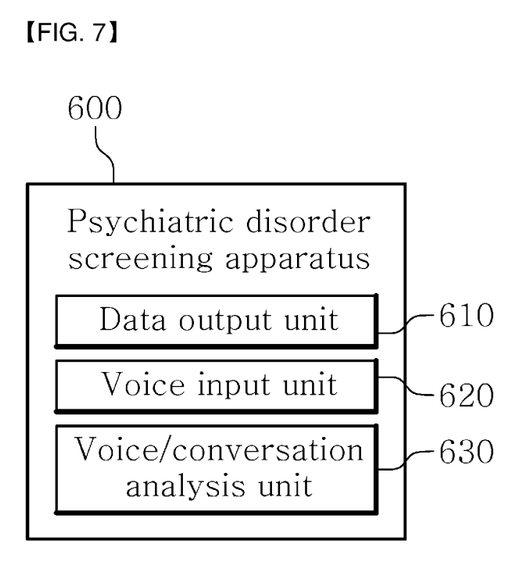
FIG. 7 shows a configuration of an example of a psychiatric disorder screening apparatus according to an embodiment of the present disclosure.

FIG. 7 is a diagram showing a configuration of an example of a psychiatric disorder screening apparatus according to an embodiment of the present disclosure.

Referring to FIG. 7, the psychiatric disorder screening apparatus 600 includes a data output unit 610, a voice input unit 620 and a voice/conversation analysis unit 630.

The psychiatric disorder screening apparatus 600 may be implemented as the user terminal 100 and the analysis server 140 connected via the network 150 as shown in FIG. 1, or may be implemented as the user terminal 140 alone. For example, the data output unit 610, the voice input unit 620 and the voice/conversation analysis unit 630 may be implemented as an application and mounted and executed on a smartphone or an AI speaker. Alternatively, the psychiatric disorder screening apparatus 600 may be implemented in various forms according to embodiments such that the data output unit 610 and the voice input unit 620 may be implemented as an application and mounted and executed on a smartphone or an AI speaker, and the voice/conversation analysis unit 630 may be implemented in the analysis server 140.

The data output unit 610 outputs stimulation. For example, in case that the data output unit 610 is implemented in an AI speaker or a smartphone, the data output unit 610 may output stimulation through the AI speaker. According to embodiments, the data output unit 610 may receive stimulation from the external analysis server 140 and output it through the AI speaker. Alternatively, the data output unit 610 may output casual question details such as date, weather or family, as the stimulation.

The voice input unit 620 receives the testee's response to the stimulation. For example, in case that the voice input unit 620 is implemented in an AI speaker, the voice input unit 620 may receive the testee's input response to the stimulation through the AI speaker.

The voice/conversation analysis unit 630 determines the presence or absence of a psychiatric disorder by analyzing the testee's input response through the voice input unit 620. For example, when the testee's response to the story stimulation of FIGS. 5 and 6 is received, the voice/conversation analysis unit 630 may analyze the testee's correct answer ratio and the testee's voice feature. According to embodiments, the voice/conversation analysis unit 630 may be implemented in the user terminal 100 or the analysis server 140 of FIG. 1. In case that the voice/conversation analysis unit 630 is implemented in the analysis server 140 of FIG. 1, the voice input unit 620 may transmit the testee's response to the analysis server 140.

In another embodiment, the voice/conversation analysis unit 630 determines the presence or absence of a psychiatric disorder by analyzing the testee's input conversation details through the voice input unit 620. For example, the voice/conversation analysis unit 630 may determine the presence or absence of a psychiatric disorder by analyzing the number of words included in the testee's response, the use or non-use of low frequency words and the usage frequency of feeling words and comparing it with a predefined reference. Alternatively, the voice/conversation analysis unit 630 may use an artificial intelligence model trained using conversation details with persons belonging to the normal group and the disease group as training data. In this case, the voice/conversation analysis unit 630 may identify which of the normal group or the disease group the conversation details with the testee belong to through the artificial intelligence model. The voice/conversation analysis unit 630 may determine the presence or absence of a psychiatric disorder using at least one of the correct answer ratio, the voice feature or the conversation details.

The present disclosure may be implemented as computer-readable code in a computer-readable recording medium. The computer-readable recording medium includes any type of recording device for storing data that can be read by a computer system. Examples of the computer-readable recording medium include ROM, RAM, CD-ROM, magnetic tape, floppy disk and optical data storage devices. Additionally, the computer-readable recording medium is distributed over computer systems connected via a network, and may store and execute the computer-readable code in a distributed manner.

The exemplary embodiments of the present disclosure have been hereinabove described. Those having ordinary skill in the technical field pertaining to the present disclosure will understood that the present disclosure may be embodied in modified forms without departing from the essential features of the present disclosure. Therefore, the disclosed embodiments should be considered in illustrative view, not in limitative view. The scope of the present disclosure is defined in the appended claims rather than the foregoing description, and all changes in the equivalent scope should be interpreted as being included in the present disclosure.

The invention claimed is:

1. A psychiatric disorder screening method based on conversation,
    the method comprising:
    outputting first stimulation including at least one of a story, a word, a sound, a picture, a motion, a color or a direction;
    receiving first response to the first stimulation from a testee and outputting second stimulation based on the first response; and
    receiving second response to the second stimulation, and calculating likelihood of psychiatric disorder of the testee by considering at least one of the testee's correct answer ratio of the first response and the second response, the testee's voice feature of the first response and the second response, or conversation details of the first response and the second response, and
    wherein outputting the first stimulation comprises changing type of the first stimulation or difficulty of the first stimulation when the correct answer ratio of the testee's the first response to the first stimulation is equal to or larger than a predetermined value.

2. The psychiatric disorder screening method based on conversation according to claim 1,
    wherein outputting the first stimulation comprises outputting a predefined other word instead of a word included in the story stimulation to increase a difference between a normal group and a disease group with regard to the stimulation.

3. The psychiatric disorder screening method based on conversation according to claim 1,
    wherein outputting the first stimulation comprises determining the stimulation to output according to response details of the testee.

4. The psychiatric disorder screening method based on conversation according to claim 1,
    wherein outputting the first stimulation comprises controlling an output interval between stimuli or placing interference stimulation in the stimulation.

5. The psychiatric disorder screening method based on conversation according to claim 1,
    wherein the voice feature includes at least one of a formant, Mel-Frequency Cepstral Coefficients (MFCCs), a pitch, a sound length or a voice quality.

6. A psychiatric disorder screening apparatus, comprising:
    a data output unit to output first stimulation including at least one of a story, a word, a sound, a picture, a motion, a color or a direction;
    a voice input unit to receive first response to the first stimulation from a testee;
    wherein the data output unit to output second stimulation based on the first response, and
    a voice analysis unit to calculate likelihood of psychiatric disorder of the testee by considering at least one of the testee's correct answer ratio of the first response and a second response, the testee's voice feature of the first response and the second response, or conversation details of the first response and the second response, and wherein the data output unit changes type of the first stimulation or difficulty of the first stimulation when the correct answer ratio of the testee's the first response to the first stimulation is equal to or larger than a predetermined value.

7. A computer-readable recording medium having computer-readable instructions stored thereon, the instructions being executed by at least one processor to enable the at least one processor to perform the steps of:

outputting first stimulation including at least one of a story, a word, a sound, a picture, a motion, a color or a direction;

receiving first response to the first stimulation from a testee and outputting second stimulation based on the first response; and receiving second response to the second stimulation, and calculating likelihood of psychiatric disorder of the testee by considering at least one of the testee's correct answer ratio of the first response and the second response, the testee's voice feature of the first response and the second response, or conversation details of the first response and the second response, wherein outputting the first stimulation comprises changing type of the first stimulation or difficulty of the first stimulation when the correct answer ratio of the testee's the first response to the first stimulation is equal to or larger than a predetermined value.

* * * * *